United States Patent [19]

Tamura et al.

[11] 4,329,462
[45] May 11, 1982

[54] PROCESS FOR PRODUCING CARBOXYLIC AMIDES

[75] Inventors: Nobuhiro Tamura, Chigasaki; Yohei Fukuoka, Kurashiki; Joji Nishikido, Fuji; Setsuo Yamamatsu, Fuji; Yoshio Suzuki, Fuji, all of Japan

[73] Assignee: Asahi Kasei Kogyo Kabushiki Kaisha, Osaka, Japan

[21] Appl. No.: 195,740

[22] PCT Filed: Aug. 1, 1979

[86] PCT No.: PCT/JP79/00201

§ 371 Date: Apr. 3, 1980

§ 102(e) Date: Mar. 28, 1980

[30] Foreign Application Priority Data

Aug. 3, 1978 [JP] Japan ................................. 53-94135

[51] Int. Cl.$^3$ ........................................... C07D 295/10
[52] U.S. Cl. ................................. 544/387; 260/239.1; 544/386; 546/245; 564/133; 564/138; 564/139; 564/141; 564/161; 564/215; 549/487
[58] Field of Search ............... 564/215, 161, 133, 138, 564/139, 141; 260/347.3, 239.1; 546/245, 317; 544/386, 387

[56] References Cited

U.S. PATENT DOCUMENTS

| | | | |
|---|---|---|---|
| 2,617,805 | 11/1952 | Wissow | 546/317 |
| 3,192,258 | 6/1965 | Nakagawa et al. | 562/538 |
| 3,226,390 | 12/1965 | Nakagawa et al. | 546/45 |
| 4,126,748 | 11/1978 | Scholz et al. | 562/538 |

FOREIGN PATENT DOCUMENTS 1130078 10/1968 United Kingdom.

OTHER PUBLICATIONS

Carruthers, Some Modern Methods of Organic Synthesis, University Press, Cambridge, 1971, pp. 251–259.
Nakagawa et al. (III), J. Org. Chem., 27 (1962), pp. 1597–1601.

*Primary Examiner*—Arthur P. Demers
*Attorney, Agent, or Firm*—Sprung, Horn, Kramer & Woods

[57] ABSTRACT

Carboxylic amides can be produced simply and in good yield by reacting primary alcohols with at least one compound selected from ammonia, primary amines, and secondary amines, in the presence of a molecular oxygen-containing gas and a palladium or platinum catalyst under oxidative conditions.

15 Claims, No Drawings

PROCESS FOR PRODUCING CARBOXYLIC AMIDES

TECHNICAL FIELD

The present invention relates to a process for producing carboxylic amides. More particularly, it relates to a process for producing carboxylic amides by oxidative reaction of primary alcohols with ammonia or an amine.

BACKGROUND ART

It is well-known that carboxylic amides, industrially useful materials, are produced by reaction of carboxylic acids or esters thereof with an amine, which reaction is applicable as a general method of making them, or hydrolysis of the corresponding nitriles. The yield in each of these processes has arrived at an almost satisfactory level owing to the recent development of the technology, but both these processes need long routes from the petroleum chemical raw materials. As an approach to shortening these routes, for instance, a method as disclosed in British Pat. No. 925588 is known, wherein reaction of carbon monoxide with dimethylamine is effected for the production of N,N-dimethylformamide; however, it requires a high pressure as well as troublesome procedure for treatment of the by-products such as formic acid and others. Consequently, development of a simpler and more economical process has been looked for in the industry.

DISCLOSURE OF INVENTION

This invention provides a process for producing carboxylic amides, characterized in that (a) a primary alcohol is allowed to react with (b) at least one compound selected from the group consisting of ammonia, primary amines, and secondary amines in the presence of (c) a molecular oxygen-containing gas and (d) a palladium or platinum catalyst. According to this invention, carboxylic amides can be produced with simplicity and convenience.

BEST MODE FOR CARRYING OUT THE INVENTION

One of the starting materials used in this invention is a primary alcohol. Examples of the primary alcohol are monohydric alcohols including saturated aliphatic primary alcohols such as methanol, ethanol, isopropyl alcohol, n-butyl alcohol, 2-ethylhexanol, and n-octyl alcohol; unsaturated aliphatic primary alcohol such as allyl alcohol and crotyl alcohol; aromatic alcohols such as benzyl alcohol and cinnamyl alcohol; heterocyclic alcohols such as pyridyl alcohols and furfuryl alcohol. The above-mentioned aromatic alcohols also include that which has been substituted in the aromatic ring by a halogen atom such as chlorine, bromine, or fluorine, by a $C_1$ to $C_5$ alkyl group such as methyl, ethyl, isopropyl, or n-amyl, by a $C_1$ to $C_5$ haloalkyl group such as chloromethyl or bromoethyl; or by an alkoxy group such as methoxy or ethoxy. The above-mentioned heterocyclic alcohols also include that which has been substituted in the heterocyclic ring by a $C_1$ to $C_5$ alkyl group such as methyl, ethyl, isopropyl, or n-amyl, or by a $C_1$ to $C_5$ haloalkyl group such as chloromethyl or bromoethyl. Also, polyhydric alcohols such as ethylene glycol, propylene glycol, glycerin, and the like may be used.

Among these primary alcohols, those excellent in respect of reactivity in the process of this invention are methyl alcohol; a primary alcohol having no hydrogen atom attached to the carbon atom next to the carbon atom to which the alcoholic hydroxyl group is attached, such as non-substituted or substituted benzyl alcohols, non-substituted or substituted pyridylcarbinols, or non-substituted or substituted furfuryl alcohols; a primary alcohol having an unsaturated bond at the carbon atom adjoining to the carbon atom to which the alcoholic hydroxyl group is attached, such as allyl alcohol or crotyl alcohol; particularly, methyl alcohol, benzyl alcohol, pyridylcarbinols, and furfuryl alcohol are most preferable.

Another starting material used in this invention is ammonia, a primary amine, or a secondary amine. The followings are the typical examples of the primary amine, but any other primary amine may be used: aliphatic primary amines such as methylamine, ethylamine, propylamine, isopropylamine, and butylamine; alicyclic primary amines such as cyclopropylamine, cyclopentylamine, and cyclohexylamine; aromatic primary amines such as aniline, toluidine, and naphthylamine; aralkyl primary amines such as benzylamine and xylylenediamine; and primary amines each having a heterocylic skeleton such as a penicilline or cephalosporine skeleton.

Examples of the secondary amine are as follows: aliphatic secondary amines such as dimethylamine, diethylamine, di-n-propylamine, and methylethylamine; aromatic secondary amines such as methylaniline and ethylaniline; and compounds each having a heterocyclic ring in which a nitrogen atom forms a secondary amine structure, such as piperidine, piperazine, pyrazoline, pyrrolidine, and pyrroline. The above-mentioned primary and secondary amines may also include an amine which has been substituted in the position of a carbon atom constructing the amine compound, by a halogen atom such as chlorine, bromine, or fluorine, by an alkyl group such as methyl, ethyl, isopropyl, or n-octyl, or by an alkoxy group such as methoxy or ethyoxy.

Among these, ammonia, the above-mentioned primary amines, dimethylamine, diethylamine, methylethylamine, piperidine, and piperazine are especially favorable, and ammonia, methylamine, ethylamine, dimethylamine, and diethylamine are most suitable.

The amount ratio of such primary alcohol to the compound selected from ammonia, primary amines, and secondary amines, may be choosed at will depending upon the reaction, but in general, the molar ratio of the latter (ammonia or the amine) to the former (the primary alcohol) is about 0.002 to about 100, and preferably not less than about 0.01.

Oxygen to be used in this invention is molecular oxygen, that is, it is possible to use either gaseous oxygen alone or in a mixture diluted with an inert gas, for example, such as gaseous nitrogen or gaseous carbon dioxide. Also, air can be used.

The amount of oxygen in the reaction system is to be not less than the stoichiometric quantity for this reaction, and its preferred and sufficient amount is about 1.5 times the stoichiometric quantity or more.

The catalyst used for operating the process of this invention is palladium or platinum, which may be applied in the form of metal by itself, but preferably in the form of metal supported on a carrier. In this case, the usual carrier such as activated carbon, silica, or alumina can be used satisfactorily. The content of the metal supported is in the range of about 0.1 to about 20% by weight, preferably in the range of about 0.5 to about 10% by weight, based on the weight of such a carrier.

Furthermore, when the catalyst contains, in addition to palladium or platinum, at least one element selected from the group consisting of lead, thallium, and mercury, it gives more excellent results than does the catalyst containing palladium or platinum, singly. These elements, lead, thallium, and mercury, may be used in the form of either metal or compound. As the compound, they may be used, for example, in the form of salts including the halogenides, the other inorganic salts, and the organic salts, as well as in the form of oxide or hydroxide. The halogenides include the chlorides, bromides, iodides, and fluorides; the other inorganic salts include the salts of sulphuric acid, nitric acid, phosphoric acid, and boric acid; the organic salts include the salts of formic, acetic, propionic, stearic, malonic, succinic, glutaric, maleic, benzoic, phthalic, etc. The amount of lead, thallium, or mercury, to be added is about 0.01 to about 30; preferably about 0.1 to about 10, in atomic ratio based on the palladium or platinum.

These catalyst may be prepared in the way being practiced usually: for instance, a carrier is immersed in aqueous solution of a palladium or platinum salt, and after drying, the metal salt is reduced to metallic state with hydrogen, hydrazine, formalin, or the like, to serve for the reaction.

The above-mentioned catalyst containing lead, thallium, or mercury, may be prepared also in the usual way wherein, for example, a carrier is added to aqueous solution of lead acetate, and after stirred for several hours to adsorb the lead acetate, the resulting mass is calcined at about 500° to about 700° C., further, it is added to aqueous solution of palladium chloride, and after several hour's stirring to adsorb palladium chloride, the resulting mass is subjected to reduction treatment with formalin, hydrazine, or hydrogen. In the case of the catalyst system containing platinum and a lead salt, it is obtained by addition of a platinum-supporting carrier to aqueous solution of a lead salt, followed by stirring and then drying.

Also in the case of the catalyst incorporated with lead, thallium, or mercury, it is preferable to use a carrier-supported catalyst, and the preferred amount of the palladium or platinum supported is in the range of about 0.1 to about 20% by weight, and the particularly preferred amount is in the range of about 0.5 to about 10% by weight, based on the carrier weight. In comparison with platinum, palladium gives better results either in the system employing each of them singly or in the system employing each of them in combination with lead, thallium, or mercury.

The reaction temperature according to this invention is preferred to be about 0° to about 200° C., or the reaction can be carried out at relatively low temperatures as about 15° to about 150° C. It is a wonder that this reaction system has oxidation reactivity in the vicinity of ordinary temperatures. Moreover, in order to solubilize the reactants, it is possible to use an inert solvent such as, for example, dimethylformamide, dioxane, or the like. The reaction can be carried out under any pressure, reduced, atmospheric, or increased, and either batchwise or continuously.

The invention is further illustrated by referring to the following examples; however, it is not limited to these examples.

EXAMPLE 1

Ten cc of aqueous solution (40 wt%) of dimethylamine, 100 cc of methanol, and 5 g of a commercial 5% palladium-carbon (made by Engelhard Corp.) as a catalyst, were placed into a 4-necked flask equipped with a gas inlet, a reflux condenser, a stirrer, and a thermometer. While thoroughly stirring the reaction mixture with the inner temperature of the flask raised to 40° C., reaction was carried out by passing air through the gas inlet into the mixture at a rate of 15 l/hr for 2 hours.

Results of analysis of the reaction mixture solution after the reaction showed that the conversion of dimethylamine was 92% and the yield of N,N-dimethylformamide was 78% based on the charged dimethylamine.

EXAMPLE 2

Using the same apparatus as used in Example 1, 50 cc of aqueous solution containing 5 g of 3-pyridylcarbinol, a species of pyridyl alcohol, together with 2 g of a commercial 5% palladium-carbon (made by Engelhard Corp.) as a catalyst was placed therein. As a result of the reaction carried out at a temperature of 50° C. for 3 hours by passing gaseous ammonia at a rate of 0.3 l/hr and air at a rate of 10 l/hr, the yield of nicotinamide was 62% based on the charged 3-pyridylcarbinol and no other products were detected by gas chromatography.

EXAMPLE 3

Ten cc of aqueous solution (40 wt%) of dimethylamine, 100 cc of ethanol, and 5 g of a commercial 5% platinum-alumina (made by Engelhard Corp.) as a catalyst, were placed into the same apparatus as used in Example 1, and reaction was carried out at a set temperature of 50° C. by passing oxygen at a rate of 2 l/hr for 4 hours.

On analyzing the reaction mixture solution after the reaction, the yield of N,N-dimethylacetamide was found to be 23%.

EXAMPLE 4

Two g of benzyl alcohol, 40 g of dioxane as a solvent, 20 g of aqueous ammonia (28%), and 2 g of an activated carbon-supported catalyst (content of palladium supported=5%, atomic ratio of Pd:Pb=1:3, form of Pb supported=PbO) were placed into a 3-necked 100 cc-flask, and reaction was carried out in the same way as Example 1, whereby the following results were obtained:

Conversion of benzyl alcohol: 75%
Yield of benzamide: 65%

EXAMPLE 5

Four g of benzyl 6-aminopenicillanate, 60 g of methanol, and 4 g of an alumina-supported catalyst (content of palladium supported=5%, atomic ratio of Pd:Pb=1:5, form of Pb supported=PbO) were placed into a 3-necked 100 cc-flask, and while thoroughly stirring the reaction mixture with the inner temperature of the flask kept at 30° C., reaction was carried out by passing air through a gas inlet into the reaction mixture at a rate of 10 l/hr for 2 hours.

The yield of benzyl 6-N-formyl penicillanate was 14%.

EXAMPLE 6

Using 2 g of furfuryl alcohol, 30 g of aqueous solution (40 wt%) of methylamine, 20 g of dioxane as a solvent, and an activated carbon-supported catalyst (content of palladium supported=5%, atomic ratio of Pd:Pb=1:3, form of Pb supported=lead acetate), reaction was carried out in the same apparatus as used in Example 1 at a reaction temperature of 40° C. by passing oxygen at a rate of 5 l/hr for 2 hours, whereby the following results were obtained.

Conversion of furfuryl alcohol: 77%
Yield of furfurylmonomethylamide: 69%

EXAMPLE 7

Two g of crotyl alcohol, 30 g of aqueous solution (40%) of methylamine, 30 g of dioxane as a solvent, and an activated carbon-supported catalyst (content of platinum supported=5%, atomic ratio of Pt:Pb=1:0.5, form of Pb supported=lead bromide) were placed into the same apparatus as used in Example 1, and reaction was carried out at a reaction temperature of 30° C. by passing oxygen at a rate of 5 l/hr for one hour. As a result, the yield of methacrylmonomethylamide was 31%.

EXAMPLE 8

Five g of diethylamine, 50 g of methanol, and 5 g of an activated carbon-supported catalyst (content of palladium supported=10%, atomic ratio of Pd:Pb=1:10, form of Pb supported=lead nitrate) were placed into a 3-necked 100 cc-flask, and while thoroughly stirring the reaction mixture with the inner temperature of the flask kept at 40° C., reaction was carried out by passing oxygen through a gas inlet into the reaction mixture at a rate of 5 l/hr for 3 hours. As a result, diethylformamide was obtained in a yield of 59% based on diethylamine.

INDUSTRIAL APPLICABILITY

According to this invention, carboxylic amides can be obtained from alcohols and amines under mild conditions in good yields as well as in one stage. Hence, this invention has extremely economical advantages.

We claim:

1. A process for producing a carboxylic amide, characterized in that a primary alcohol is allowed to react with at least one compound selected from the group consisting of ammonia, primary amines, and secondary amines, in the presence of a molecular oxygen-containing gas and a palladium or platinum catalyst.

2. A process for producing a carboxylic amide according to claim 1, characterized in that said primary alcohol is at least one compound selected from the group consisting of methanol, a primary alcohol having no hydrogen atom attached to the carbon atom next to the carbon atom to which the alcoholic hydroxyl group is attached, and a primary alcohol having an unsaturated bond at the carbon atom adjacent to the carbon atom to which the alcoholic hydroxyl group is attached.

3. A process for producing a carboxylic amide according to claim 2, wherein said primary alcohol is at least one compound selected from the group consisting of methyl alcohol, benzyl alcohol, pyridylcarbinol, and furfuryl alcohol.

4. A process for producing a carboxylic amide according to claim 1, wherein the process comprises reacting a primary alcohol and at least one compound selected from the group consisting of ammonia, primary amines, dimethylamine, diethylamine, methylethylamine, piperidine, and piperazine.

5. A process for producing a carboxylic amide according to claim 1, wherein the compound selected from the group consisting of ammonia, primary amines, and secondary amines, is ammonia, methylamine, ethylamine, dimethylamine, or diethylamine.

6. A process for producing a carboxylic amide according to claim 1, wherein the palladium or platinum catalyst is metallic palladium or metallic platinum, supported on a carrier.

7. A process for producing a carboxylic amide according to claim 1, wherein the palladium or platinum catalyst contains, in addition to palladium or platinum, at least one element selected from the group consisting lead, thallium, and mercury.

8. A process for producing a carboxylic amide according to claim 7, wherein the palladium or platinum catalyst containing, in addition to palladium or platinum, at least one element selected from the group consisting of lead, thallium, and mercury, is supported on a carrier.

9. A process for producing a carboxylic amide according to claim 6 or 8, wherein the content of palladium or platinum supported on a carrier is about 0.1 to about 20% by weight based on the weight of the carrier.

10. A process for producing a carboxylic amide according to claim 9, wherein the content of palladium or platinum supported on a carrier is about 0.5 to about 10% by weight base on the weight of the carrier.

11. A process for producing a carboxylic amide according to claim 1, wherein the catalyst is palladium or platinum containing at least one element selected from the group consisting of lead, thallium, and mercury.

12. A process for producing a carboxylic amide according to claim 1, wherein at least one compound selected from the group consisting ammonia, primary amines, and secondary amines, is used in an amount ratio of about 0.002 to about 100 moles per one mole of the primary alcohol.

13. A process for producing a carboxylic amide according to claim 1, wherein the reaction temperature is about 15° to about 200° C.

14. A process for producing a carboxylic amide according to claim 13, wherein the reaction temperature is about 15° to about 150° C.

15. A process for producing a carboxylic amide according to claim 11, wherein the atomic ratio of lead, thallium or mercury to palladium or platinum ranges from about 0.01 to 30.

* * * * *